United States Patent [19]

Serdar

[11] Patent Number: 5,589,386
[45] Date of Patent: Dec. 31, 1996

[54] HYDROLYSIS OF CHOLINESTERASE INHIBITORS USING PARATHION HYDROLASE

[76] Inventor: Cuneyt M. Serdar, 1844 Rivendell Cir., Newbury Park, Calif. 91320

[21] Appl. No.: 312,503

[22] Filed: Feb. 17, 1989

Related U.S. Application Data

[63] Continuation-in-part of Ser. No. 237,255, Aug. 26, 1988.

[51] Int. Cl.$^6$ .......................... C12S 13/00; C12N 15/00; C12N 1/20; C12N 1/14
[52] U.S. Cl. ................... 435/262.5; 435/172.3; 435/195; 435/252.3; 435/252.33; 435/254.11; 435/254.21; 435/814; 435/815; 935/14; 935/29; 935/56
[58] Field of Search ..................... 435/172.3, 196, 435/874, 262.5, 195, 252.3, 252.33, 254.11, 254.21, 814, 815; 935/14, 29, 56

[56] References Cited

U.S. PATENT DOCUMENTS 4,391,887   7/1983   Baumgarten et al. .................. 435/874

OTHER PUBLICATIONS

Munnecke et al., Eur. J. Appl. Microbiol. Biotechnol., vol. 8, Nos. 1–2, pp. 103–112 (1979).
Serdar et al., Bio/Technology, vol. 3, No. 6, pp. 567–571 (1985).
Mulbry et al., Appl. Environ. Microbiol., vol. 51, No. 5, pp. 926–930 (1986).
Attaway et al., Appl. Environ, Microbiol., vol. 53, No. 7, pp. 1685–1689 (1987).
Mulbry et al., Plasmid, vol. 18, No. 2, pp. 173–177 (1987).
McDaniel et al., J. Bacterial., vol. 170, No. 5, pp. 2306–2311 (May, 1988).
Harper et al., Appl. Environ. Microbiol., vol. 54, pp. 2586–2589 (1988).

*Primary Examiner*—David M. Naff
*Attorney, Agent, or Firm*—Steven M. Odre

[57] ABSTRACT

A gene is provided encoding a DNA sequence for the expression of parathion hydrolase and a methionine analog thereof. In a preferred embodiment, a parathion hydrolase gene encoding sequence is obtained in which twenty-eight amino acids are deleted from the N-terminal amino acid sequence of parathion hydrolase. Parathion hydrolase or its analog is produced by transforming a host microorganism such as Escherichia, Bacillus or Streptomyces with the gene, culturing the microorganism in a culture medium and purifying parathion hydrolase therefrom. Highly purified soluble parathion hydrolase is produced by a purification method without using detergents such as Triton X-100 and Tween 20. Parathion hydrolase of enhanced activity is produced by adding cobalt or zinc or a mixture thereof to the culture medium in which the host microorganism is cultured. The parathion hydrolase is useful for hydrolyzing organophosphorus compounds such as the cholinesterase inhibitors, diisopropylphosphoro-fluoridate, pinacolylmethylphosphono-fluoridate and isopropylmethylphosphono-fluoridate.

4 Claims, 8 Drawing Sheets

```
481  CGATTGAGGAGTGTAGAGGAACTCACACAGTTCTTCCTGCCTGAGATTCAATATGGCATC
         +         +         +         +         +         +    540
     ArgLeuArgSerValGluGluLeuThrGlnPhePheLeuArgGluIleGlnTyrGlyIle

541  GAAGACACCGGAATTAGGGCGGGCATTATCAAGGTCGCGACCACAGGCAAGGCGACCCCC
         +         +         +         +         +         +    600
     GluAspThrGlyIleArgAlaGlyIleIleLysValAlaThrThrGlyLysAlaThrPro

601  TTTCAGGAGTTAGTGTTAAAGGCCGCCCCCGGCCAGCTTGGCCACCGGTGTTCCGGTA
         +         +         +         +         +         +    660
     PheGlnGluLeuValLeuLysAlaAlaAlaArgAlaSerLeuAlaThrGlyValProVal

661  ACCACTCACACGGCAGCAAGTCAGCGCGATGGTGAGCAGCAGGCCCCCATTTTTGAGTCC
         +         +         +         +         +         +    720
     ThrThrHisThrAlaAlaSerGlnArgAspGlyGluGlnAlaAlaIlePheGluSer

721  GAAGGCTTGAGCCCCTCACGGGTTTGTATTGGTCACAGCGATGATACTGACGATTTGAGC
         +         +         +         +         +         +    780
     GluGlyLeuSerProSerArgValCysIleGlyHisSerAspAspThrAspAspLeuSer
                                                        XbaI

781  TATCTCACCGCCGCTGCCGCGGATACCTCATCGTTCTAGACCACATCCCGCACAGT
         +         +         +         +         +         +    840
     TyrLeuThrAlaLeuAlaAlaArgGlyTyrLeuIleGlyLeuAspHisIleProHisSer
        XbaI

841  GCGATTGGTCTAGAAGATAATGCGAGTGCATCAGCCGCATCCTCGGCCATCCGTTCGTGCAA
         +         +         +         +         +         +    900
     AlaIleGlyLeuGluAspAsnAlaSerAlaLeuLeuGlyIleArgSerTrpGln
                 BclI

901  ACACGGGCTCTCTGATCAAGGCGCTCATCGACCAAGGCTACATGAAACAAATCCTCGTT
         +         +         +         +         +         +    960
     ThrArgAlaLeuLeuIleLysAlaLeuIleAspGlnGlyTyrMetLysGlnIleLeuVal
```

FIG. 6B

```
481  CGATTGAGGAGTGTAGAGGAACTCACACAGTTCTTCCTGCTGTGAGATTCAATATGGCATC
          +         +         +         +         +         + 540
     ArgLeuArgSerValGluGluLeuThrGlnPhePheLeuArgGluIleGlnTyrGlyIle

541  GAAGACACCGGAATTAGGCGGGCATTATCAAGGTCGCGACCACAGGCAAGGCGACCCCC
          +         +         +         +         +         + 600
     GluAspThrGlyIleArgAlaGlyIleIleLysValAlaThrThrGlyLysAlaThrPro

601  TTTCAGGAGTTAGTGTTAAAGGCGGCCCCCGGGCCCAGCTTGGCCACCGGTGTTCCGGTA
          +         +         +         +         +         + 660
     PheGlnGluLeuValLeuLysAlaAlaAlaArgAlaSerLeuAlaThrGlyValProVal

661  ACCACTCACACGGCAGCAAGTCAGCCGATGTGGTGAGCAGCAGGCCCGCCATTTTGAGTCC
          +         +         +         +         +         + 720
     ThrThrHisThrAlaAlaSerGlnArgAspGlyGluGlnAlaAlaIlePheGluSer

721  GAAGGCTTGAGCCCCTCACGGGTTTGTATTGGTCACAGCGATGATACTGACGATTTGAGC
          +         +         +         +         +         + 780
     GluGlyLeuSerProSerArgValCysIleGlyHisSerAspThrAspAspLeuSer
                                                   XbaI

781  TATCTCACCGCCCCTCGCTGCGCGGATACCTCATCGGTCTAGACCACATCCCGCACAGT
          +         +         +         +         +         + 840
     TyrLeuThrAlaLeuAlaAlaArgGlyTyrLeuIleGlyLeuAspHisIleProHisSer
     XbaI

841  GCGATTGGTCTAGAAGATAAATGCGAGTGCATCAGCCCTCGGGCATCCGTTCGTGGCAA
          +         +         +         +         +         + 900
     AlaIleGlyLeuGluAspAsnAlaSerAlaLeuGlyIleArgSerTrpGln
                BclI

901  ACACGGGCTCTCTGATCAAGGCGCTCATCGACCAAGGCTACATGAAACAAATCCTCGTT
          +         +         +         +         +         + 960
     ThrArgAlaLeuLeuIleLysAlaLeuIleAspGlnGlyTyrMetLysGlnIleLeuVal
```

```
961  TCGAATGACTGGCTGTTCGGGTTTTCGAGCTATGTCACCAACATCATGGACGTGATGGAT
     SerAsnAspTrpLeuPheGlyPheSerSerTyrValThrAsnIleMetAspValMetAsp
                                                      DdeI

1021 CGCGTGAACCCCGACGGGATGGCCCTTCATTCCACTGAGAGTGATCCCCATTCCTACGAGAG
     ArgValAsnProAspGlyMetAlaPheIleProLeuArgValIleProPheLeuArgGlu

1081 AAGGGGCGTCCCACAGGAAACGCTGGCAGGCATCACTGTGACTAACCCGGCGGGTTCTTG
     LysGlyValProGlnGluThrLeuAlaGlyIleThrValThrAsnProAlaArgPheLeu
                                               BamHI

1141 TCACCGACCTTGCGGGCCGTCATGACGCCATCTGGATCCTTCCAGCCAGCGGCACTATTC
     SerProThrLeuArgAlaSerEnd

1201 CCCGTCAAGATACCGAACGATGAAGTCGCGCATCGATAGGCATCTTCAATTTGATC

1261 AGGGCTGCCACCTCCAAAGCCGTGGCCACCCCTGTCGATAGTCTTGAGGACGTAGGGCAC
                                  PstI  3'
1321 ACCGTGCTTTTCGAACTGCAG
                    + 1341
```

HYDROLYSIS OF CHOLINESTERASE INHIBITORS USING PARATHION HYDROLASE

This is a continuation-in-part of Ser. No. 237,255 filed Aug. 26, 1988, now abandoned, hereby incorporated by reference.

The present invention provides a novel gene encoding DNA sequence for the expression of parathion hydrolase and an analog thereof, and a method for preparing such compounds. Other synonyms for parathion hydrolase include organophosphorus acid anhydrase parathion aryl esterase, and phosphotriesterase. In a particularly preferred embodiment, the present invention relates to a parathion hydrolase gene encoding sequence in which twenty-eight amino acids are deleted from the N-terminal amino acid sequence of parathion hydrolase. The novel gene encoding parathion hydrolase encoding sequence is useful for production of the mature or processed parathion hydrolase and a methionine (−1) analog thereof.

BACKGROUND

Parathion (0,0-diethyl-O-p-nitrophenyl phosphorothioate) was discovered in 1944 by Schrader (Eto, M., 1974 organophosphorus pesticides: organic and biological chemistry, CRC Press Inc., Cleveland, Ohio). It is an organophosphate pesticide that is extremely toxic to higher organisms because parathion (PAR) is converted by the cytochrome P-450 monooxygenase system to paraoxon which is a potent acetylcholinesterase inhibitor (Taylor, The pharmacological basis of therapeutics, 6th ed. pp. 100–119 (1980)).

Organophosphate pesticides applied to agricultural environments at recommended rates are not extremely persistent. However, when higher concentrations of PAR are applied to soil samples, persistence increases, and PAR can be detected in some soils after 16 years (Wolfe et al., Bull. Environ. Contam. Toxicol. 10:1–9 (1973)). It has been estimated that the remaining pesticide residue in pesticide containers is approximately $4.5 \times 10^5$ kilograms per year (Munnecke, Process Biochem. 13:16–19 (1978)). The major source of pesticide discharges occurs at pesticide production and formulation plants, which release more than $4 \times 10^5$ kilograms of pesticides each year (Munnecke, supra (1978)). Therefore, hazards exist with respect to undesirable discharges such as pesticide containers, production plants, or accidental spills (Munnecke, Microbial degradation of xenobiotics and recalcitrant compounds, Academic Press Inc., London, pp. 251–270 (1981)). In these instances, clean-up procedures are required. Enzymes which can decrease the toxicity of the pesticide molecule by a simple hydrolysis reaction could possibly be used for the detoxification of residual pesticides at these industrial point sources.

1. Microbial Degradation of Organophosphates and Possible Industrial Applications Over millions of years, microorganisms have evolved the ability to utilize many compounds as sole sources of carbon and energy (Gibson et al., Microbial degradation of organic compounds, Marcel Dekker, Inc. New York (1984)). The importance of the studies of microbial metabolism is exemplified by the virtue of microorganisms as the major means by which many chemical pollutants are eliminated from a variety of ecosystems.

The vast majority of the 500 or so active pesticidal chemicals can be biologically degraded by fungal or bacterial microorganisms. General reviews discussing microbial metabolism of pesticides have been edited by Bollag, Advan. in Appl. Microbiol. 18:75–130 (1974), and Laveglia and Dahm, Annu. Rev. Entomol. 22:483–513 (1977).

Figure 1:
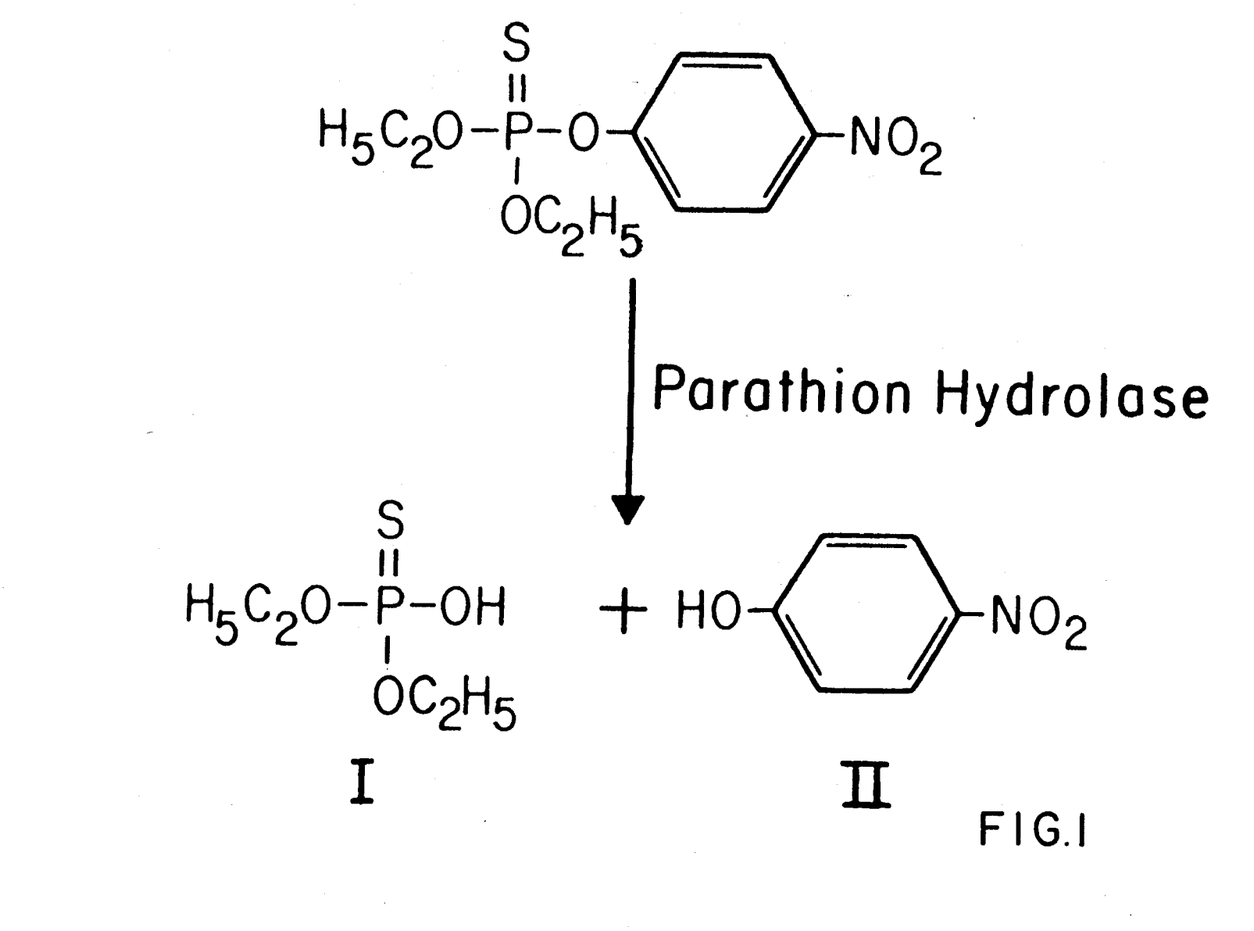
FIG. 1 depicts the hydrolysis of parathion. (Prior Art)

Munnecke and Hsieh, Appl. Environ. Microbiol. 31:63–69 (1976) have studied the degradation of parathion by a mixed microbial culture and found the major metabolites to be p-nitrophenol and diethylthiophosphoric acid (FIG. 1). Hydrolysis of parathion reduces its toxicity by nearly 120-fold and releases water-soluble metabolites that are more available to further microbial degradation. p-nitrophenol can be further utilized as a source of carbon and energy by other microorganisms (Munnecke and Hsieh, Supra: Simpson, Biochem, J. 55:xxiv (1953); and Spain et al., Biochem. Biophys. Res. Commun. 88:634–641 (1979)). Another study has shown that diethylthiophosphoric acid is utilized as the sole phosphorus source by some soil microorganisms (Cook et al., Appl. Environ. Microbiol. 36:668–672 (1978)).

A cell-free enzyme preparation obtained by Munnecke from a mixed bacterial culture hydrolyzed the organophosphate insecticides ethyl parathion, methyl parathion, paraoxon, diazinon, dursban, EPN, cyanophos, fenitrothion, and triazophos at rates significantly higher than chemical hydrolysis with sodium hydroxide (Munnecke, Appl. Environ. Microbiol. 32:7–13 (1976)). The enzyme activity for pesticide hydrolysis was stable at temperatures up to 45°–50° C. and had a temperature and pH optimum for expression of enzymatic activity of 35° C. and pH 8.5–9.0, respectively (Munnecke, supra (1976)).

Parathion is enzymatically hydrolyzed to diethylthiophosphoric acid (I) and p-nitrophenol (II) by parathion hydrolase for *P. diminuta* MG (pCMS1) (FIG. 1).

The enzymatic removal of PAR from pesticide containers has been demonstrated (Munnecke, Agric. Food Chem. 28:105–111 (1980)). It was observed that within 16 hours, 94% of the residual PAR present in the drums as a 48% emulsifiable concentrate was hydrolyzed after parathion hydrolase was added.

The feasibility of using enzyme preparations to clean up soil spills has been demonstrated in both laboratory and field conditions. Work by Barik and Munnecke, Bull. Environm. Contam. Toxicol. 29:235–239 (1982) has shown that parathion hydrolase can hydrolyze diazinon in soil. More than 98% of 1% diazinon in the soil was removed within 24 hours when sufficient amounts of buffer and enzyme were added to the contaminated soil. This concentration of pesticide would normally remain in untreated soil for many years (Wolfe et al., supra). In greenhouse studies, soil samples were treated with different concentrations of diazinon (Honeycutt et al., ACS Symposium Series, No. 259, Treatment & Disposal of Pesticide Wastes, pp. 343–352 (1984)). Parathion hydrolase was added to the soil samples to determine the efficacy of the enzyme to rapidly degrade diazinon during a spill situation. The half-life of diazinon in the 500 ppm treatment without enzyme present was 9.4 days, while the half-life of diazinon in the 500 ppm treatment with enzyme present was one hour. These studies indicate that parathion hydrolase can be used effectively to rapidly reduce large concentrations of diazinon in soil.

Investigations using a mixed microbial culture that converts PAR to PNP led to the isolation of *Pseudomonas diminuta* strain MG which contains high levels of parathion hydrolase activity (Serdar et al., Appl. Environ. Microbiol.

44:246–249 (1982)). In all cases, parathion hydrolase activity was produced in the absence of added PAR. On the basis of these results, it appears that parathion hydrolase was produced constitutively by this organism. *P. diminuta* MG and a Flavobacterium sp. (ATCC 27551), isolated by Sethunathan and Yoshida, Can. J. Microbiol. 19:873–875 (1973), are the most extensively studied organisms that degrade organophosphates.

2. Plasmids Involved in Organophosphate Degradation

Plasmids are extrachromosomal genetic elements that code primarily for nonessential functions yet enable certain organisms to survive in unique ecological niches. Many unusual metabolic activities of Pseudomonas species are plasmid-encoded functions (Haas, Experentia, 39:1199–1213 (1983)).

To determine whether parathion hydrolase activity was controlled by a plasmid, attempts have been made to correlate loss of PAR hydrolase activity with plasmid removal. Expression of enzymatic activity was lost at a frequency of approximately 12% after treatment with mitomycin C (Serdar, supra (1982)). Hydrolase-negative derivatives were lacking a plasmid present in the wild-type organism. These cured colonies differed phenotypically from the parent strain only in inability to hydrolyze PAR. These results suggested that PAR hydrolase activity may be mediated by plasmid DNA, although induction of deletion mutations could not have been excluded.

This plasmid designated as pCMS1 was determined to be 66 kilobase (kb) in size by using electron microscopy (Serdar, supra (1982)). Recent studies using restriction mapping have confirmed the molecular size estimate (Mulbry et al., Appl. Environ. Microbiol. 51:926–930 (1986)). This is the first example of plasmid involvement in the degradation of an organophosphorus compound.

More recently it was shown that the Flavobacterium sp. ATCC 27551 contains a 39 kb plasmid, pPDL2, that is involved in the degradation of organophosphates (Mulbry et al., supra (1986); and Mulbry et al., Plasmid 18:173–177 (1987)). The gene encoding parathion hydrolase (termed opd, organophosphate-degrading gene) from pCMS1 was shown to be homologous to that located in pPDL2, as determined by DNA-DNA hybridization and restriction mapping. Further DNA hybridization studies have revealed that these plasmids share homology only within an approximately 5.1 kb region of DNA (Mulbry et al., supra (1987)).

3. Construction of Recombinant Plasmids Containing the Parathion Hydrolase Gene

Two cloning stategies were employed (Serdar and Gibson, Bio/Technology 3:567–571 (1985)). One method was the use of different restriction endonuclease sites of pBR322 (Bolivar et al., Gene. 2:95–113 (1977)). for 'shot-gun' cloning with subsequent studies for parathion hydrolase expression in *E. coli*. The other procedure utilized the EcoRI site of the broad host range vector, pKT230 (Bagdasarian et al., Gene. 16:237–247 (1981)); recombinant plasmids generated using pKT230 can be mobilized into Pseudomonas strains using a helper plasmid, pRK2013 (Figurski et al., Proc. Natl. Acad. Sci. USA. 76:1648–1652 (1979)).

Following the cloning experiment using pKT230 as the vector, two transformants that hydrolyzed PAR were isolated, and each was shown to contain a hybrid plasmid with an identical 6.0 kilobase EcoRI insert (Serdar, supra (1985)). This plasmid was designated as pCMS29 as shown in FIG. 2.

Figure 2:
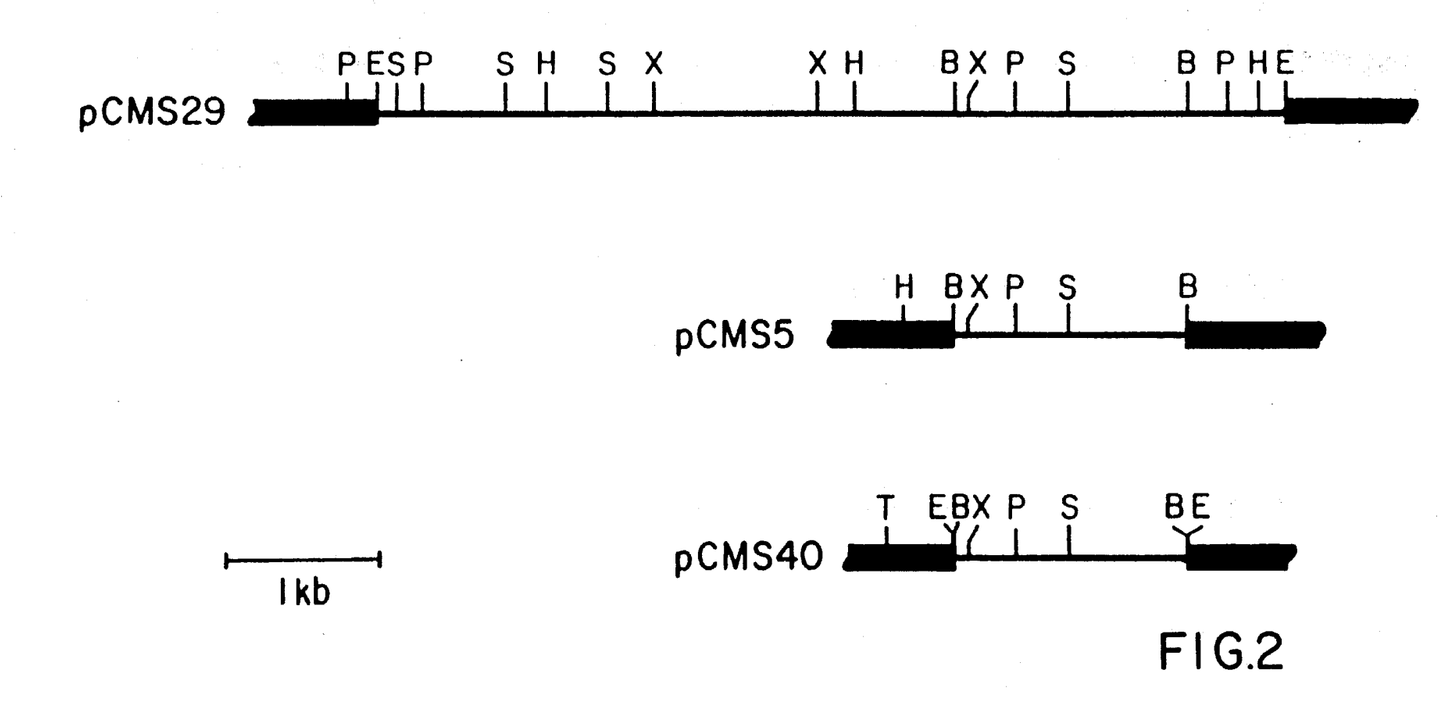
FIG. 2 shows the physical maps of recombinant plasmids carrying the parathion hydrolase gene of *P. diminuta* MG (pCMS1). (Prior Art)

FIG. 2 represents the physical maps of the recombinant plasmids carrying the parathion hydrolase gene of *P. diminuta* MG (pCMS1). The thick lines represent the adjacent portions of vector DNA; the thin lines represent the inserted pCMS1 DNA fragments. Restriction endonucleases used were: B, BamHI; E, EcoRI; H, HindIII; P, PstI; S, SalI; T, TaqI; X, XhoI.

Alternative cloning procedures utilized the BamHI, HindIII and SalI restriction sites of the vector pBR322. DNA fragments produced from pCMS1 by these restriction enzymes were ligated into similarly treated pBR322 and were used to transform *E. coli* HB101. A BamHI-generated clone which hydrolyzed PAR was shown to contain a hybrid plasmid designated as pCMS5 (FIG. 2). Analysis by restriction endonuclease digestion revealed that this plasmid contained a 1.5 kb insert. In contrast, parathion hydrolase activity was not detected in any of the transformants containing hybrid plasmids constructed with SalI.

In order to increase the synthesis of parathion hydrolase in *E. coli* and to construct a 1.5 kb fragment suitable for inserting into the EcoRI site of the plasmid pKT230, the 1.5 kb BamHI fragment located in pCMS29 was subcloned into the high expression vector pUC7 (Vieira et al., Gene. 19:259–268 (1982)). This resulting strain contained a plasmid, designated as pCMS40, with a 1.5 kb insert which was flanked by the EcoRI sites of pUC7. Restriction maps of the 6.0 kb EcoRI fragment in pCMS29, the 1.5 kb BamHI fragment in pCMS5, and the subcloned 1.5 kb BamHI fragment in pCMS40 are shown in FIG. 2.

Plasmids suitable for studying the expression of the parathion hydrolase gene in Pseudomonas strains were constructed by EcoRI cleavage of pCMS40 and subsequent ligation into EcoRI cleaved pKT230.

TABLE I

| Parathion hydrolase activity* (Prior Art) | |
|---|---|
| Strain | Activity |
| *P. diminuta* MG | ND |
| *P. diminuta* MG (pCMS1) | 2.1 |
| *P. diminuta* MG (pCMS29) | 4.8 |
| *P. diminuta* MG (pCMS55) | 9.2 |
| Pseudomonas strain 24 | ND |
| Pseudomonas strain 24 (pCMS29) | 0.03 |
| Pseudomonas strain 24 (pCMS55) | 0.07 |
| *E. coli* strains | |
| HB101 (pBR322) | ND |
| BHB2600 (pKT230) | ND |
| JM105 (pUC7) | 0.002 |
| BHB2600 (pCMS29) | 0.002 |
| HB101 (pCMS5) | 0.03 |
| JM105 (pCMS40) | 0.19 |
| BHB2600 (pCMS55) | 0.004 |
| BHB2600 (pCMS60) | ND |

*Activity has been converted from nanomoles to micromoles (μmol) of parathion hydrolyzed per minute per milligram of protein. ND, not detected.

Figure 3:
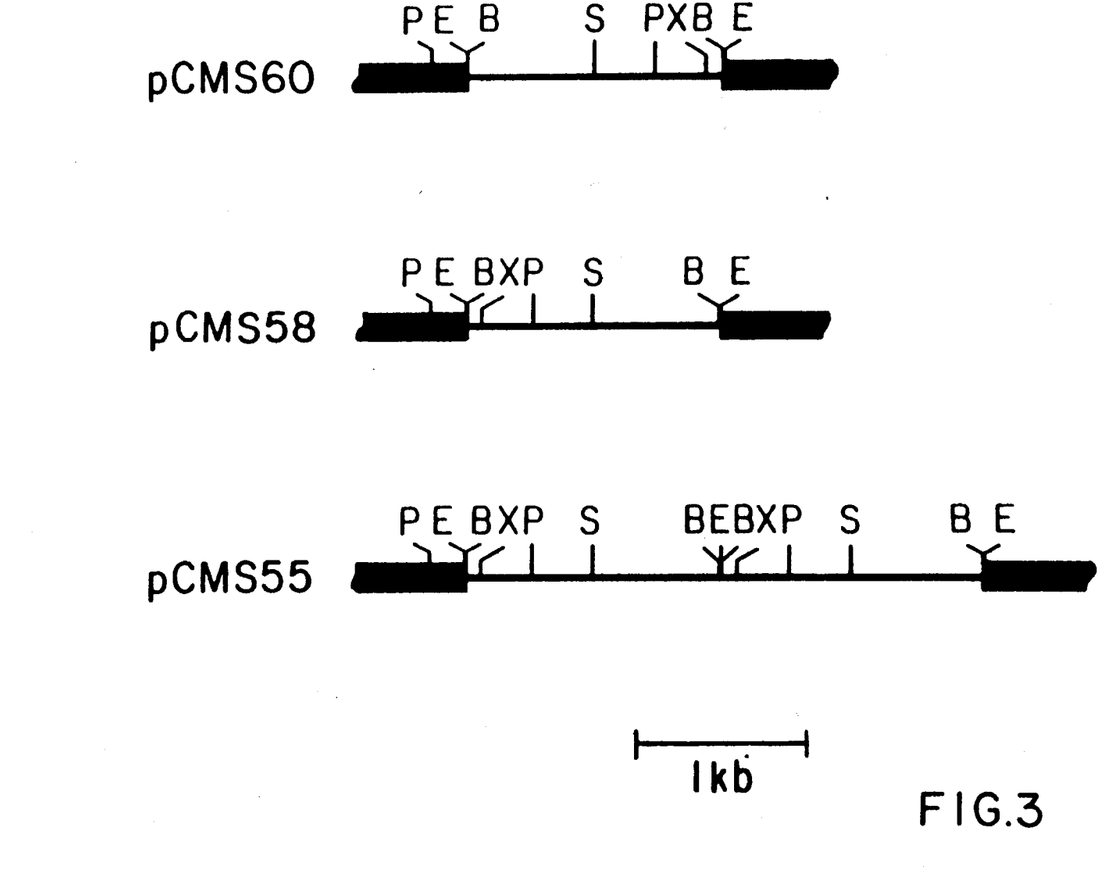
FIG. 3 shows the physical maps of KT230 derivatives containing the parathion hydrolase in different orientations. (Prior Art).

*E. coli* BHB2600 cells transformed with plasmids designated pCMS55 and pCMS58 showed enzymatic activity, and each plasmid contained the 1.5 kb BamHI insert. The highest parathion hydrolase activity was associated with pCMS55 which contained two 1.5 kb inserts in the same orientation relative to the vector as shown in FIG. 3. Further screening led to the isolation of an additional strain that contained a plasmid (pCMS60) with the same 1.5 kb insert in the opposite orientation. However, this strain showed no parathion hydrolase activity. FIG. 3 represents the physical maps of pKT230 derivatives containing the parathion hydrolase gene in different orientations. The heavy lines correspond to the pKT230 DNA; the thin lines show the inserted pCMS1 DNA. Restriction endonucleases used were: B, BamHI; E, EcoRI, P, PstI; S, SalI; X, XhoI.

Of particular interest to the background of the present invention is McDaniel et al., J. Bacteriol., 170:2306, 1988, which published a DNA sequence of a 1.32 kb PstI fragment from *P. diminuta* MG plasmid, pCMS1. McDaniel et al. observed the total number of base pairs (bp) to be 1322. According to their analysis the stop codon (TGA) was located at the unique Dde1 site within the parathion hydrolase gene at 1038 bp. The open reading frame was determined to be 975 bp. McDaniel et al. constructed several subclones: two clones extended the 3'-end to approximately 675 bp and 840 bp. These strains, containing either clone, had no enzymatic activity. Another construct was deleted at the 5'-end SalI site (353 bp) which also did not contain activity.

McDaniel et al. concluded that the parathion hydrolase enzyme was not soluble and was associated with the particulate fraction of lysed *P. diminuta* cells. They suggested that the enzyme was released from the particulate fraction upon treatment with detergents such as Triton X-100 or Tween 20. From their evaluation of elution fractions from Sephadex G-200 column chromatography, they concluded that the molecular weight of the enzyme was 60–65 kilodaltons (kd). From their molecular weight determinations, McDaniel et al. suggested that the enzyme exists in its active form as a dimer. The McDaniel et al. article provides no evidence that the enzyme produced is processed parathion hydrolase.

To date, a correct gene encoding sequence for unprocessed parathion hydrolase has not been described. In particular, no gene encoding sequence for processed parathion hydrolase has been described or suggested.

SUMMARY OF THE INVENTION

Figure 6B:
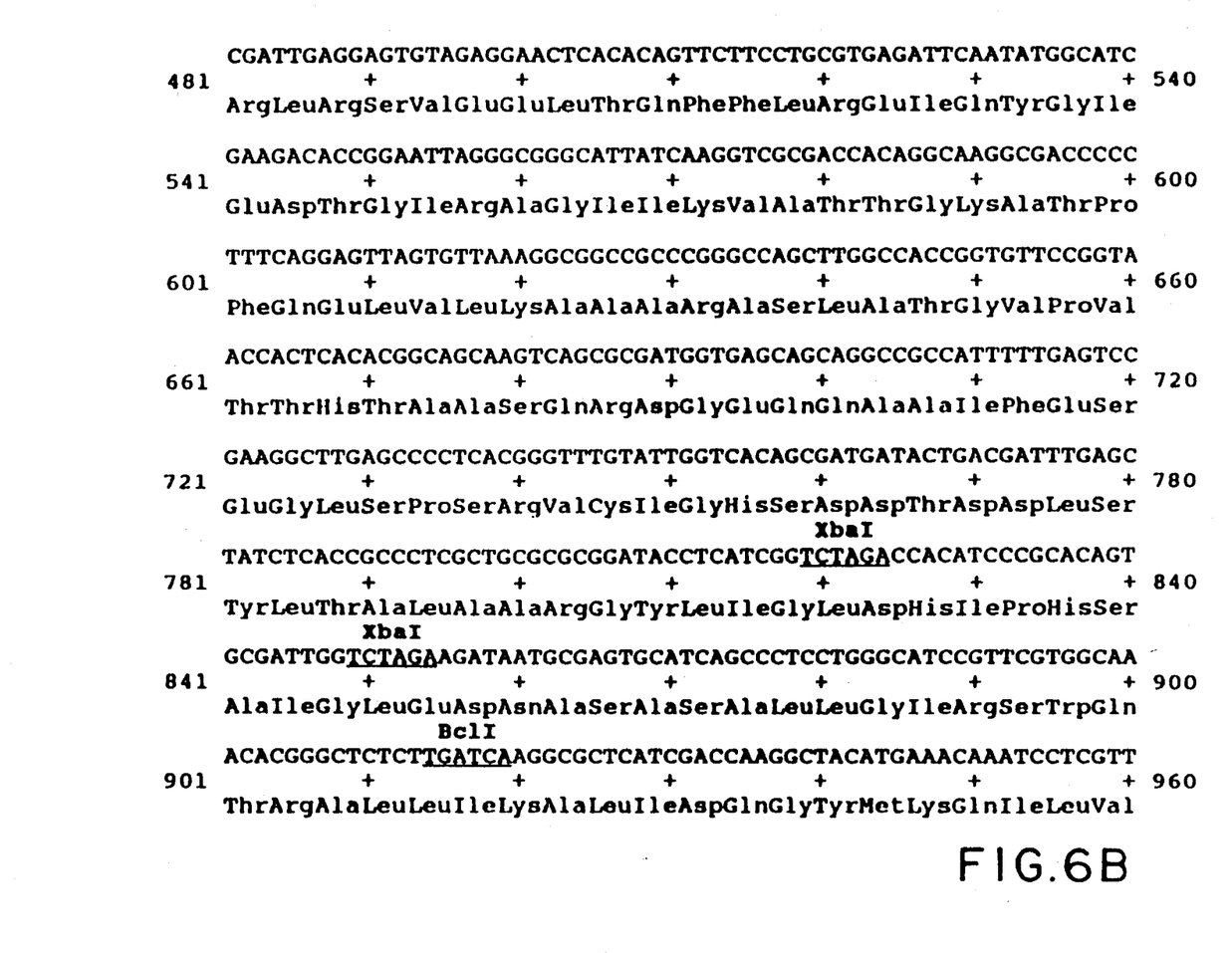
FIG. 6 shows the nucleotide sequence of the 1.34 Kb PstI fragment.
Figure 6C:
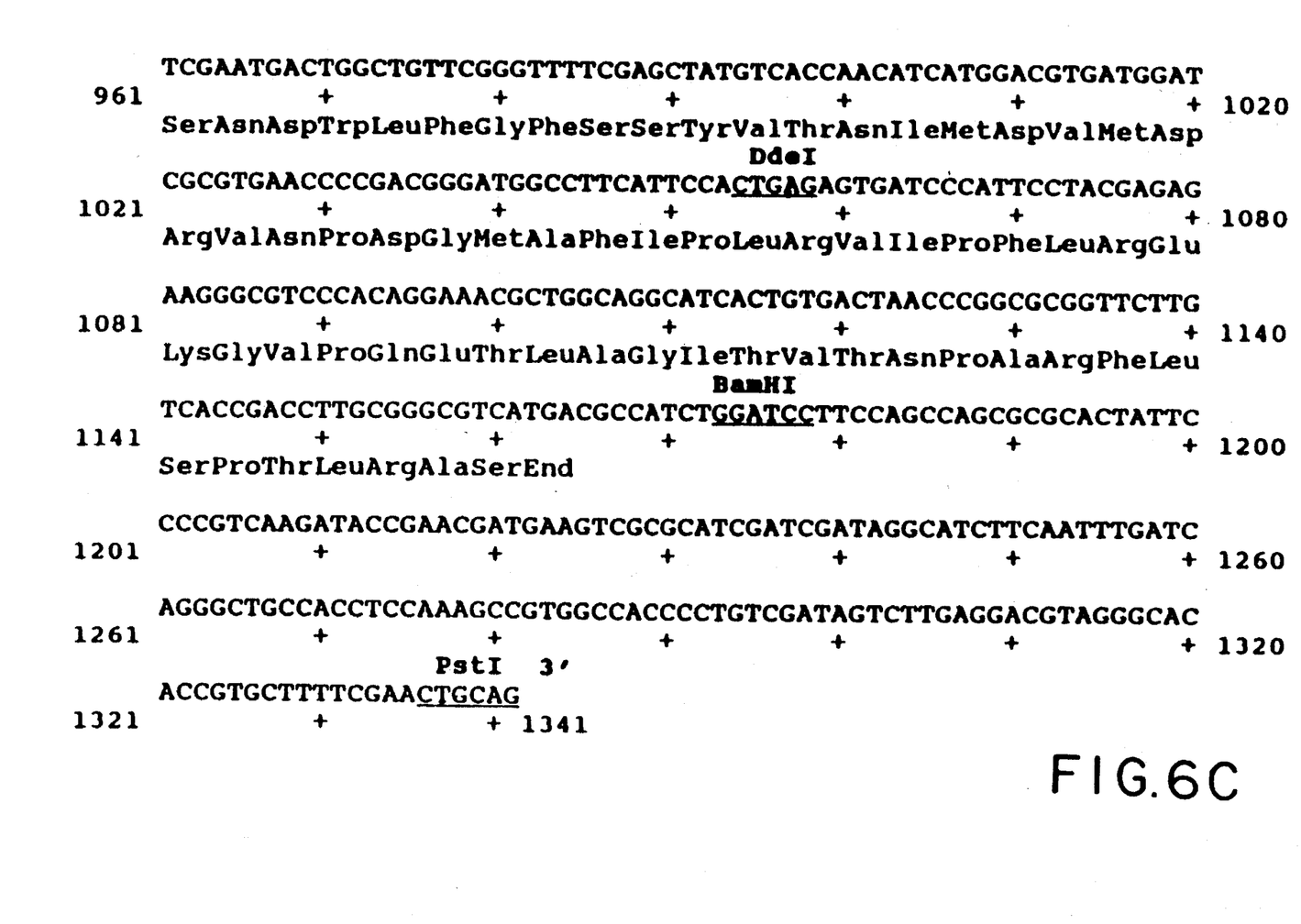

It should be noted that, as employed herein, the term parathion hydrolase refers to compounds derived from a wild-type strain or having host cell systems having the amino acid sequence as shown in FIG. 6. The gene encoding sequence for parathion hydrolase, as shown in FIG. 6, starts at position 67 bp and provides an unprocessed parathion hydrolase product having a molecular weight of approximately 39 kd as indicated by SDS-polyacrylamide gel electrophoresis (SDS-PAGE). The term processed parathion hydrolase refers to a compound derived from a host cell system having a gene encoding sequence as shown in FIG. 6. The gene encoding sequence as shown in FIG. 6 starts at position 154 bp and provides a processed parathion hydrolase product having a molecular weight of approximately 36 kd as indicated by SDS-PAGE.

The present invention provides higher purity of processed parathion hydrolase that is obtained from crude or partially purified extracts. This is the first demonstration of obtaining a high level of parathion hydrolase activity in an alternative host system such as *E. coli*.

The present invention provides processed parathion hydrolase in soluble form in commercial quantities that is stable.

The present invention provides a gene encoding sequence for expression or production of processed parathion hydrolase and a methionine (−1) analog thereof. The present invention also provides an industrially feasible recombinant process for preparing high levels of active and stable processed parathion hydrolase. The gene encoding sequence and analogs thereof, according to the present invention, are generally characterized by the deletion of twenty-nine amino acids from the N-terminal amino acid sequence of parathion hydrolase.

The processed parathion hydrolase product of the present invention has an amino acid sequence wherein the N-terminal amino acid sequence of the processed parathion hydrolase starts with serine at the 30th position. Alternatively, the processed parathion hydrolase is a methionine (−1) analog.

A nucleic acid according to the present invention has codons encoding a polypeptide analog as described above.

A system for the production of processed parathion hydrolase according to the present invention comprises a host cell in turn comprising nucleic acid encoding a processed parathion hydrolase or a methionine (−1) analog thereof. In such a cell, the nucleic acid encoding the processed parathion hydrolase or analog may be chromosomal or extrachromosomal. The host cell is preferably selected from the group consisting of *E. coli*, Bacillus and Streptomyces.

An object of the present invention is to provide a process for producing high activity levels of processed parathion hydrolase according to the system described above which further includes the addition of metals such as Cobalt (Co) and Zinc (Zn) in sufficient amounts to increase the activity of enzyme greater than 20 fold. In a preferred embodiment, amounts of >0.1 mM of cobalt and/or zinc have significantly increased the activity of enzyme.

Yet a further object of the present invention is to provide a method of purification of soluble and processed parathion hydrolase in the absence of detergents such as Triton X-100 and Tween 20.

Further aspects and advantages of the present invention will become apparent upon consideration of the following detailed description of presently preferred embodiments thereof.

DETAILED DESCRIPTION

The methods and materials which provide an illustration of the invention and which comprise the presently preferred embodiment relate to a gene encoding sequence which can be employed in the production of processed parathion hydrolase.

The invention is now illustrated by the following Examples, with reference to the accompanying drawings. The examples do not include detailed descriptions for conventional methods employed in the isolation of DNA, the cleavage of DNA with restriction enzymes, the construction of vectors, the insertion of DNA gene segments encoding polypeptides of interest into such vectors (e.g. plasmids), or the introduction of the resulting recombinant plasmids into microorganism host cells. Such methods are well known to those skilled in the art of genetic engineering and are described in numerous publications including the following: Maniatis et al., *Molecular Cloning—A Laboratory Manual*, pCFM526 plasmid contains a heat inducible promoter, a restriction site bank (cloning cluster), plasmid origin of replication, a transcription terminator, genes regulating plasmid copy number, gene conferring ampicillin resistance, and a synthetic ribosome binding site immediately preceeding the cloning cluster. The pAC1 plasmid was derived from pCFM526 by substituting the DNA sequence between the unique AatII and ClaI restriction sites with the following oligonucleotide.

AatII

CAGATCCATAAATTATCTCTGGCGGTGTTGACATAAATACCACTGGCGGTGATAA—

TGCAGTCTAGGTATTTAATAGAGACCGCCACAACTGTATTTATGGTGACCGCCACTATT—

ClaI

—TGAGCACAT

—ACTCGTGTAGC

Cold Spring Harbor Laboratory (1982); Davis et al., *Basic Methods in Molecular Biology*, Elsevier Science Publishing Co. (1986); *Current Protocols in Molecular Biology*, edited by Ausubel et al., Greene Publishing Associates and Wiley Interscience (1987).

Figure 4:
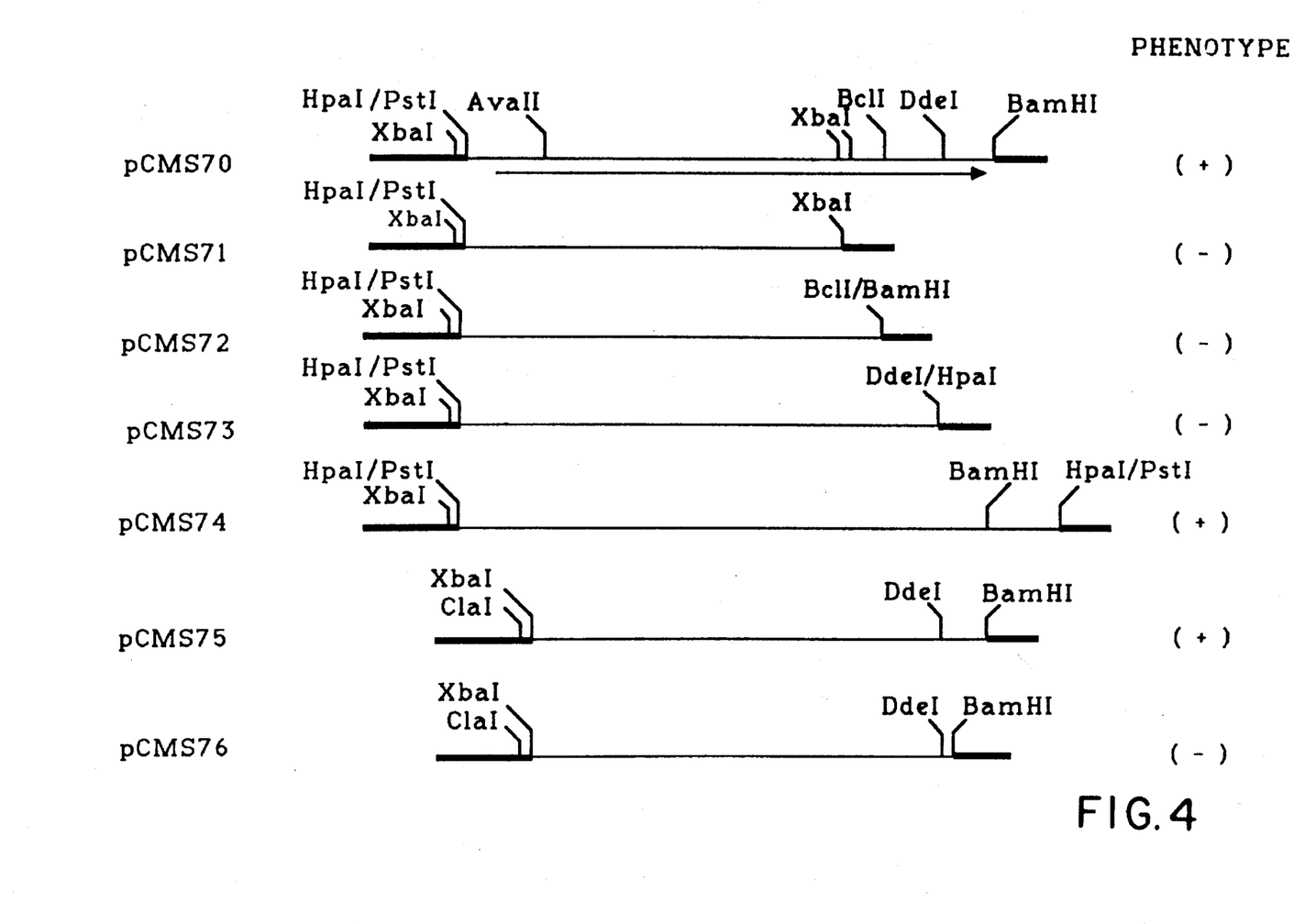
FIG. 4 shows a linear map of the recombinant plasmids of the present invention.

In order to determine the correct gene encoding sequence for unprocessed parathion hydrolase, a series of plasmids were constructed to determine the correct location of the parathion hydrolase gene within the pCMS1 DNA. It should be noted that in contrast to the constructs of McDaniel et al., supra, that did not yield enzyme activity, the following constructs were constructed to specifically determine the proper identification of the coding region. Plasmids pCMS70, pCMS71, pCMS72, pCMS73, and pCMS74 consist of pCMS1 DNA, extending from the PstI site to BamHI, XbaI, BclI, DdeI and PstI sites, respectively, as shown in FIG. 4. The linear map of the recombinant plasmids constructed in this study are shown in FIG. 4. Only relevant restriction sites used for subcloning are indicated. The thick lines represent the adjacent portions of vector DNA; the thin lines represent the inserted DNA. The arrow indicates the direction of transcription and the extent of the parathion hydrolase gene as determined by DNA sequence analysis. It includes a functional mapping of the parathion hydrolase gene and the phenotype of the strains containing these plasmids as indicated: (+) crude cell extracts contain parathion hydrolase activity, (−) crude cell extracts do not contain parathion hydrolase activity. These fragments were constructed to identify the coding region and to confirm the DNA sequence results. None of the strains containing plasmids where the 3'-end was terminated at the 818 bp XbaI site (pCMS71), 913 bp BclI site (pCMS72), 1054 bp DdeI site (pCMS73) and at 1089 bp (extended from the DdeI site using a linker, pCMS76) showed any enzyme activity.

The plasmids constructed to determine the boundaries of the coding region and to confirm the DNA sequence data are as follows:

Construction of pAC1 plasmid vector

The starting material for the construction of the pAC1 plasmid was the pCFM526 plasmid. A detailed description of the construction of expression vectors, including pCFM526, is described in U.S. Pat. No. 4,710,473, which is hereby incorporated by reference in its entirety. The This was performed by digesting pCFM526 with AatII and ClaI and isolating from agarose gel a 4.0 kb fragment which was ligated to the above oligonucleotide.

pCMS70

A 1200 bp PstI to BamHI fragment containing the parathion hydrolase gene was released from the plasmid pCMS40 and was cloned into Amgen vector pAC1. The cloning was done by digesting pCMS40 with PstI and treating with Klenow to blunt the PstI sticky ends. The DNA was digested with BamHI following phenol extraction. The pAC1 vector was digested with HpaI, phenol extracted, and then digested with BamHI. Both insert and vector DNAs were isolated from agarose gel and ligated. The resulting plasmid was designated as pCMS70.

pCMS71

The pCMS70 plasmid was digested with XbaI. Since an XbaI site is located in the pAC1 vector 10 bp upstream from the PstI/HpaI junction, a 830 bp fragment was released from the plasmid. Plasmid pAC1 DNA was digested with XbaI and treated with phosphotase. Both the vector and 830 bp insert DNAs were isolated from agarose gel and ligated. The resulting correctly oriented plasmid was designated as pCMS71.

pCMS72

Plasmid pCMS70 DNA was transformed into Damstrain of *E. coli* GM119 (CGSC Strain #6475) to cleave the BclI site. Plasmid DNA obtained from this strain was then digested with BclI and BamHI in order to eliminate a 260 bp fragment from the 3' end of the plasmid. The remaining plasmid DNA was isolated from agarose gel and religated to itself. This plasmid was designated as pCMS72.

pCMS73

The pCMS70 DNA was digested with ClaI and BamHI releasing a 1200 bp insert which was isolated from agarose gel. This DNA was then digested with DdeI releasing a 115 bp of DNA from the 3' end of the gene. The digest mixture was treated with Klenow and digested with EcoRI to eliminate a 50 bp fragment from the 5'end of the DNA insert. This treatment gave rise to a 1050 bp EcoRI/DdeI blunt ended DNA fragment. Plasmid pAC1 vector DNA was digested with HpaI and EcoRI. Both vector and insert DNAs were isolated from agarose gel and ligated. The resulting plasmid was designated as pCMS73.

pCMS74

This plasmid was constructed by isolating a 1.34 Kb PstI fragment from pCMS29 (Serdar, supra 1985). Following the Klenow treatment to form blunt ends, this fragment was inserted into HpaI digested pAC1 by ligation. Correct orientation was confirmed by restriction mapping of clones having parathion hydrolase activity.

pCMS76

This construct was made by first digesting the pCMS75 (described below) DNA with ClaI/BamHI double digest and isolating the 1100 bp insert from agarose. This insert DNA was then digested with DdeI yielding a 960 bp ClaI/DdeI fragment which was isolated from agarose gel. Plasmid pAC1 was digested with ClaI/BamHI double digest and isolated from agarose gel. A synthetic oligomer was designed with 5' DdeI and 3' BamHI sticky ends. The internal codons were kept the same as the original sequence, and a TAG termination codon was placed after the valine codon (pos. 1089). The resulting plasmid was designated as pCMS76.

DNA sequence of parathion hydrolase gene

Figure 5:
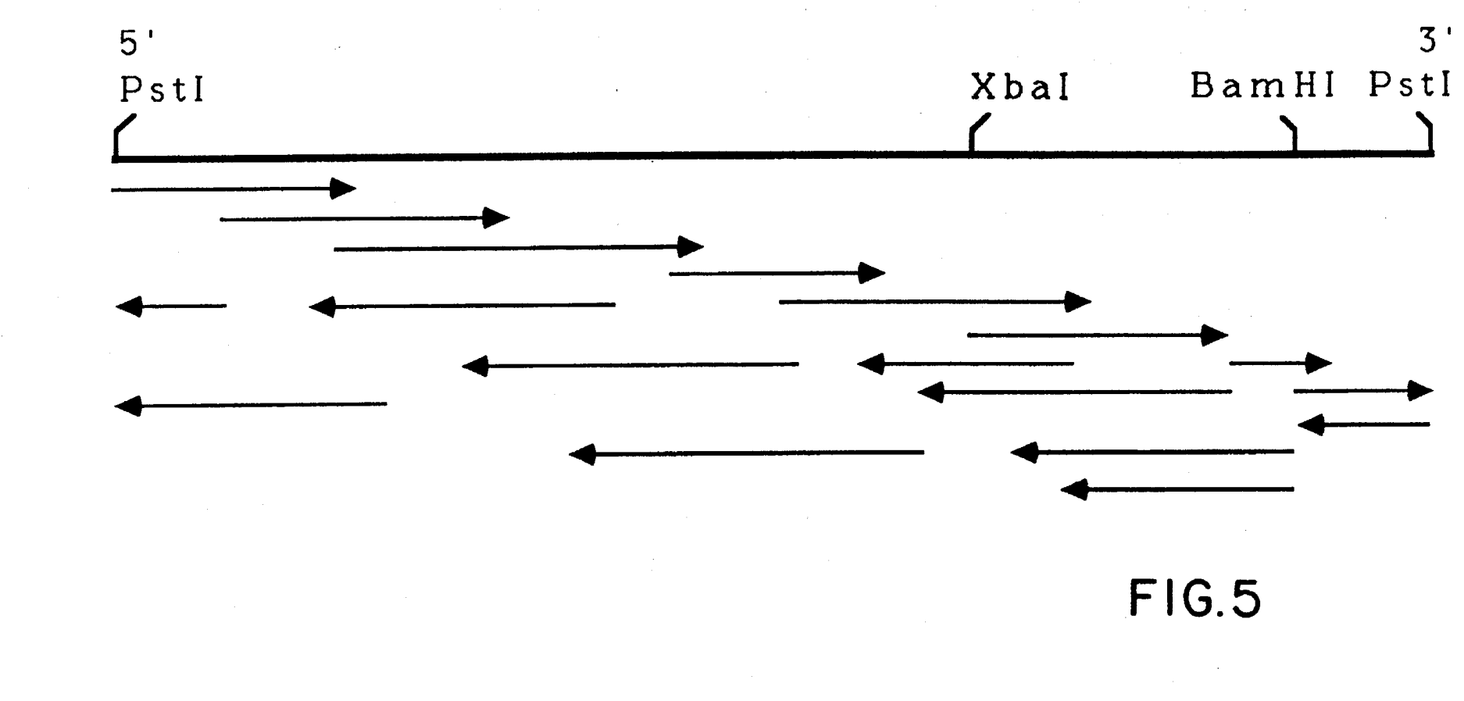
FIG. 5 shows the sequencing strategy of the 1.34 Kb PstI fragment.

To reveal the exact coding region, the 1.34 kb PstI fragment in plasmid pCMS74 was sequenced as shown in FIG. 5. The relevant restriction map, sequencing strategy, and subclones constructed for sequencing is indicated with restriction sites used for sequencing or subcloning. Arrows represent the direction and extent of the sequences obtained by using fragments produced by restriction enzyme digestion at the sites indicated or sequences obtained using synthetic oligonucleotides as primers.

The sequence disclosed a single open reading frame with an initiation codon located near the PstI site. Although, McDaniel et al., supra, believed the total number of base pairs to be 1322, the PstI fragment is 1341 base pairs as shown in FIG. 6. The nucleotide sequence of the 1.34 kilobase PstI fragment of pCMS1 containing the parathion hydrolase gene is indicated. The sequence shown is 5'→3'. The deduced amino acid sequence of the parathion hydrolase gene product is given below the DNA sequence. The sequences were determined in both directions by the Sanger method (Sanger, F. et al., Proc. Natl. Acad. Sci. USA 74:5463–5467 (1977); Heidecker, G., et al., Gene 10:69–73 (1980)). Relevant restriction sites are indicated. The experimentally determined N-terminal amino acid sequences are also double underlined.

The coding region (open reading frame) is 1095 bp, starting at an ATG site located 67 bp from the PstI site. The stop codon (TGA) was located at 1162 bp which is 103 bp downstream of the unique DdeI site (1054 bp) within the parathion hydrolase gene. This site is 8 bp upstream of the BamHI site located at 1173 bp.

A construct of the parathion hydrolase gene based on the results of the N-terminal amino acid sequence was generated. Purified parathion hydrolase (see example 2) was used for N-terminal amino acid analysis. Protein sequence analyses were performed by automated Edman degradation in an ABI 470A gas-phase microsequenator (Hewick, R. M, et al., J. Biol. Chem. 256; 7990–7997 (1981); Hunkapiller, M. W. et al., Meth. Enzymol. 91:399–413 (1985) The N-terminal amino acid sequence was identified as:

Ser-Ile-Gly-Thr-Gly-Asp-Arg-Ile-Asn-Thr-Val-Arg-Gly-Pro-Ile

Preferred Embodiments

Preferred embodiments of novel plasmids of the invention include plasmid pCMS75 which was deposited with the American Type Culture Collection, on Aug. 25, 1988 and designated A.T.C.C. No. 67778; and pCMS77 which was deposited with the American Type Culture Collection, on Aug. 25, 1988 and designated A.T.C.C. NO. 67779. The insert in the expression vector consisting of the BamHI site at the 3'-end contained parathion hydrolase activity.

pCMS75

Plasmid pAC1 was digested with XbaI/BamHI and the fragment was isolated from agarose gel. The ClaI/BamHI fragment that was released by ClaI/BamHI double digest of the pCMS70 plasmid was isolated from agarose gel and subsequently digested with AvaII. This resulted in a 990 bp AvaII/BamHI DNA fragment which was isolated from agarose gel. A synthetic linker was designed with 5' XbaI and 3' AvaII sticky ends. The linker was designed to allow proper spacing between the XbaI site of the pAC1 expression vector and the ATG start site. The ATG codon was followed by a serine codon originally located at the 154 bp position. In addition, E. coli codon usage was utilized in this linker. The resulting plasmid obtained from the ligation of these DNA fragments was designated pCMS75.

linker

XbaI                                               AvaII

CTAGATGTCTATCGGTACCGGTGACCGTATCAACACCGTTCGTG

TACAGATAGCCATGGCCACTGGCATAGTTGTGGCAAGCACCAG

It should be noted that the DNA sequence of the XbaI-AvaII polylinker includes changes in the DNA sequence for E. coli codon usage. These alternative DNA sequences provide the identical amino acid sequence as the DNA sequence of the Pseudomonas in the same region.

The processed parathion hydrolase is obtained in a soluble form and a molecular weight which corresponded with SDS-PAGE data of approximately 36 Kd.

pCMS77

Plasmid pAC1 was digested with ClaI/BamHI and the 4.4 kb fragment was isolated from agarose gel. The 1.1 kb ClaI/BamHI fragment that was released by ClaI/BamHI double digest of the pCMS70 plasmid was isolated from agarose gel and subsequently digested with AvaII. This resulted in a 990 bp AvaII/BamHI DNA fragment which was isolated from agarose gel. A synthetic linker was designed using a ribosomal binding (Shine-Delgarno) DNA sequence that is different from that used in pCMS75. This oligonucleotide, shown below, contains flanking 5' ClaI and 3'AvaII sites.

ClaI

CGATTTGATTCTAGAAGGAGGAATAACATATGTCTATCGGTACCGGTGACCGTA—

TAAACTAAGATCTTCCTCCTTATTGTATACAGATAGCCATGGCCACTGGCAT-

AvaII

—TCAACACCGTTCGTG

—AGTTGTGGCAAGCACCAG

E. coli codon usage was utilized following the methionine codon, ATG, through the AvaII site. The ATG codon was followed by a serine codon originally located at the 154 bp position. This site was identified to be the first amino acid in the N-terminal amino acid sequence of the processed enzyme.

Plasmid pCMS77, not shown in FIG. 4, is identical to pCMS75, with the exception of the DNA sequence in the regulatory region of the vector pAC1. This change is too small to become apparent in restriction maps such as those in FIG. 4.

However, such an alteration will enable the formation and aggregation of parathion hydrolase in inclusion bodies rather than in soluble form.

E. coli FM5 cells harboring pCMS77 were grown and induced in an identical manner to E. coli FM5 (pCMS75) cells (Example 1). In contrast to E. coli (pCMS75) cells which contained no inclusion bodies the E. coli (pCMS77) cells, had 3–4 large inclusion bodies per cell.

SDS-PAGE analysis to determine the proteins found in inclusion bodies was performed. Samples prepared from different fractions of cell lysate were analysed by SDS-PAGE.

Results confirmed the observation that E. coli (pCMS77) yields large amounts of parathion hydrolase which is located in inclusion bodies.

Parathion hydrolase activity of these strains were assayed as described. A ten-fold higher activity was observed using the crude cell extract of E. coli (pCMS75), as compared to the crude cell extract of E. coli (pCMS77).

It is well known that when proteins in cells form an aggregate such as inclusion bodies, the protein may be inactive and require additional processing to obtain proper folding. Therefore, one would anticipate a decrease in specific activity of the crude extract.

EXAMPLE 1

The present example relates to the effect of metals on parathion hydrolase activity.

Although trace metals may include $CoCl_2.6H_2O$ or $ZnCl_2$ concentration of 0.015 mM, the addition of larger amounts (i.e. 10-fold increase) of $CoCl_2.6H_2O$ and/or $ZnCl_2$ result in increased specific activity.

Shaker flask experiments were performed using 0.4 liters of BHI medium (Brain Heart Infusion, Difco) containing 100 µg/ml ampicillin. Flasks were supplemented with 1 mM Ca, Cd, Co, Mn, Mg and/or Zn. The cells were grown at 30° C. to an $OD_{600}$ (optical density at 600 nm)=0.4–0.5. Parathion hydrolase activity was induced by raising the culture temperature to 42° C. for 1 h and lowering the temperature back to 30° C. to continue incubation for another 4 h.

Following growth and induction, cells were centrifuged and resuspended in 20 mM Tris-HCl buffer, pH 8.5, and lysed using a French press (10,000 psi). The supernatant obtained from 30 min centrifugation at 7,000× g was used for enzyme assays. (Enzyme assays were performed according the procedure in Serdar and Gibson, Bio/Technology, 3:570 (1985). Additional concentrations of 0.2 mM and 2.0 mM $CoCl_2$ were performed. As indicated in Table II, addition of Co and/or Zn greatly increases the specific activity of parathion hydrolase.

TABLE II

| Sample | Specific Activity* |
|---|---|
| Control - no addition of metal | 2.0, 2.3, 3.0 |
| 1 mM $CaCl_2 2H_2O$ | 0.8, 1.9 |
| 1 mM $CdCl_2.5H_2O$ | 0.4, 1.0 |
| 1 mM $MgCl_2 6H_2O$ | 1.0, 2.1 |
| 1 mM $MnCl_2 4H_2O$ | 3.1, 5.5 |
| 1 mM $ZnCl_2$ | 11.5, 19.3 |
| 0.2 mM $CoCl_2 6H_2O$ | 9.8, 15.7 |
| 1.0 mM $CoCl_2 6H_2O$ | 43.2, 46.2, 48.2, 59.0 |
| 2.0 mM $CoCl_2 6H_2O$ | 18.2, 43.2 |

*Specific Activity is expressed in µmol min/mg of protein. The different values correspond to different runs.

Fed-batch fermentation was performed in a 15-liter Biolafitte fermentor. Overnight cultures were inoculated to a final $OD_{600}$ of 0.2–0.3 and fermented at 30° C. in a 8.0 liter medium consisting of 3.0 mM $CoCl_2 6H_2O$, mineral salts, trace metals, vitamins, yeast extract and glucose as the carbon source. Cells were induced at an $OD_{600}$=30 by raising the temperature to 42° C. for 1 h followed by 30° C. incubation by feeding, pH stabilization (pH 7.0) and agitation until $OD_{600}$ reached approximately 60. Cells were harvested, and the parathion hydrolase activity was determined as previously described. The concentration of $CoCl_2 6H_2O$ supplemented in this medium is approximately 200-fold greater than normally found in the trace metals solution added to the fermentation medium.

In this experiment, parathion hydrolase activity of 60 µmol/min/mg of protein was obtained from an 8.0 liters of cell culture.

EXAMPLE 2

The present example relates to the purification of parathion hydrolase.

Cultures of P. diminuta (pCMS55) (Serdar, Supra, 1985) were grown in TYE-broth (1 percent Bactotryptone, 0.5 percent Bacto-Yeast Extract). Antibiotics were used at the following final concentrations (µg/ml); Kanamycin sulfate (Km), 50. The cultures were maintained at 30° C. and grown to an $OD_{600}$=8.0. The cultures were aerated by shaking at 150 rpm.

The following purification method provides highly purified parathion hydrolase as compared to prior art crude and partial purification methods. A 60–70% purity is demonstrated at the Affi Gel Blue Gel elution step, and a greater than 95% homogeneity is obtained following elution using a sephadex G75 column. The following procedure eliminates the need for detergents such as Tween 20 and Triton X-100.

Cells of *P. diminuta* (pCMS55) were centrifuged and resuspended in 20 mM Tris-HCl buffer, pH 8.5, (1.0 g cells per 3.0 ml of buffer) and broken by passage through a French pressure cell. The supernatant obtained from 7,000 Xg centrifugation for 30 min. was further centrifuged at 100,000 Xg for 90 min to give clear crude cell extract.

The cell extract was then applied to the top of a DEAE-Sepharose column. Elution with Tris-HCl buffer gave a solution that contained parathion hydrolase since it does not bind to this column but results in the elimination of many other proteins from the cell extract. The column eluate was applied to the top of an Affi Gel Blue Gel column. The column was washed with three bed volumes of Tris-HCl buffer. Bound proteins including parathion hydrolase were eluted with linear gradient of NaCl (0.0–0.5M) in Tris-HCl buffer.

Fractions containing parathion hydrolase were pooled and concentrated by ultrafiltration using UM-10 membrane. The concentrated preparation of parathion hydrolase was loaded onto a superfine Sephadex G75 column. Elution was carried out with 20 mM Tris-HCl, pH 8.5. Fractions were collected and assayed for parathion hydrolase activity.

Parathion hydrolase can be purified to over 95% homogeneity using this procedure.

EXAMPLE 3

The present example relates to the hydrolysis of cholinesterase inhibitors by parathion hydrolase.

Hydrolysis of cholinesterase inhibitors such as DFP, Sarin and Soman by parathion hydrolase was determined by fluoride ion production. The structures of these cholinesterase inhibitors are as follows:

The enzyme preparation used in this study was partially purified parathion hydrolase having a specific activity of 1000 μmol of parathion hydrolyzed per min per mg of protein. The protein concentration of the sample was 10 mg/ml.

METHODS

Two buffers were used. The pH 7 buffer was 390 mM in KCl, 40 mM in NaCl, and 20 mM in PIPES. The pH 8.5 buffer was the same in KCl and NaCl, but 20 mM in TRIS. The pH was adjusted with HCl and KOH. The $F^-$ sensitive electrode (Orion 96-09) was standardized daily with one or another of these buffers made $2 \times 10^{-5}$M and $2 \times 10^{-4}$M in NaF.

The three substrates—DFP, Sarin, and Soman—were prepared as 0.01M solutions in double distilled water, stored at −70° C., and brought to 0° C. when ready for use. The enzyme preparation was diluted 200- to 4000-fold in appropriate buffer.

A typical determination of enzyme activity using 3 mM Soman as the substrate was as follows:

A 10 ml reaction vessel with stirring bar was charged with 3.4 ml pH 7 buffer, and the $F^-$ electrode was lowered to within 1 mm of the spinning bar; 1.5 ml 0.01M Soman was added. In about 3 min, the room temperature of 22°–24° was attained (determined in trial runs with a thermocouple). Recording was then begun with a stopwatch in cum/split mode. When a low and constant $F^-$ release was attained (usually 5–10 min), 100 μl of the 1–200 diluted enzyme sample was added and recording was continued for another 10–20 min or until not more than 6–8% of the substrate was hydrolyzed. Subtraction of the non-enzymatic slope from the gross slope shows a net enzymatic $F^-$ change. From this, an enzymatic rate of μmoles of Soman hydrolyzed per min per ml (or per mg) of undiluted enzyme preparation was calculated.

Where other additions were made (see Table III) small volumes and relatively high concentrations were used so that the added substances could be in contact with the enzyme for 30 min prior to the assay, and then during the assay, at a constant concentration.

The results in the following Tables (III, IV, V) clearly indicate that parathion hydrolase hydrolyzes other organophosphorus compounds such as DFP, Sarin and Soman. The divalent cations tested in this study caused a relatively small (10–20%) inhibition of Soman enzymatic hydrolysis (Table III). Most similar enzymes are stimulated 2- to 20-fold by $Mn^{2+}$. EDTA caused 40% inhibition (Table III) at a concentration that would have caused virtually complete inhibition of Soman or DFP hydrolysis by superficially similar enzymes from the squid or from various other microbial and animal sources (Hoskin et al., 1988. Biol. Bull. 175:305). Parathion hydrolase demonstrated the highest activity for Sarin hydrolysis when compared with the activities obtained using purified squid or the obligate thermophile enzyme.

All of the other enzyme sources—mammalian or microbial, partially purified or not—show Soman/DFP hydrolysis ratios of 5–50 (Hoskin et al., 1984. Fundam. Appl. Toxicol. 4(2):165–172), and one, an obligate thermophile does not hydrolyze DFP at all (Chettur et al., 1988. Fundam. Appl. Toxicol. 11:373–380). This ratio of Soman/DFP hydrolysis can be as high as 900-fold (Tables III and V) for parathion hydrolase indicating it has unique properties compared to the previously studied enzymes having activities.

TABLE III

| | | Hydrolysis of Soman by Parathion Hydrolase | | |
|---|---|---|---|---|
| [Soman], | | | Hydrolysis | μmol/min/ |
| mM | pH | Additions | μmoles min$^{-1}$ ml$^{-1}$ | mg |
| 5 | 7 | none | 182 | 18.2 |
| 3 | 7 | none | 94, 129 | 9.4, 12.9 |
| 3 | 8.5 | none | 152 | 15.2 |
| 3 | 7 | $5 \times 10^{-4}$M Co$^{2+}$ | 82 | 8.2 |
| 3 | 7 | $5 \times 10^{-4}$M Mn$^{2+}$ | 90 | 9.0 |
| 3 | 7 | $5 \times 10^{-4}$M Zn$^{2+}$ | 98 | 9.8 |
| 3 | 7 | $10^{-4}$M EDTA | 67 | 6.7 |
| 2 | 7 | none | 92 | 9.2 |
| 2 | 8.5 | none | 101 | 10.1 |
| 0.5 | 7 | none | 19.5, 27 | 2.0, 2.7 |
| 0.5 | 7 | $5 \times 10^{-4}$M Co$^{2+}$ | 17 | 1.7 |

TABLE IV

Hydrolysis of Sarin by Parathion Hydrolase

| [Sarin], mM | pH | Hydrolysis μmoles min$^{-1}$ ml$^{-1}$ | μmol/min/mg |
|---|---|---|---|
| 4 | 7 | 1140 | 114.0 |
| 3 | 7 | 1850 | 185.0 |
| 3 | 8.5 | 1600 | 160.0 |
| 1.6 | 7 | 1310 | 131.0 |
| 1.6 | 8.5 | 580 | 58.0 |
| 0.5 | 7 | 540 | 54.0 |
| 0.4 | 7 | 580 | 58.0 |

TABLE V

Hydrolysis of DFP by Parathion Hydrolase

| [DFP], mm | pH | Hydrolysis μmoles min$^{-1}$ ml$^{-1}$ | | μmol/min/mg | |
|---|---|---|---|---|---|
| 3 | 7 | 4,700 | 4,867 | 470.0 | 486.7 |
| 3 | 8.5 | 139,000 | 128,000 | 13,900.0 | 12,800.0 |
| 0.5 | 7 | 3,920 | 4,250 | 392.0 | 425.0 |
| 0.5 | 8.5 | 67,000 | 67,000 | 6,700.0 | 6,700.0 |

What is claimed is:

1. A method for the hydrolysis of a cholinesterase inhibitor comprising an organophosphate, said method comprising treating the cholinesterase inhibitor with a purified and isolated biologically active substance selected from the group consisting of mature parathion hydrolase and a methionine (−1) analog thereof, said parathion hydrolase having enhanced specific activity as a result of having been produced in a microorganism cultivated in a culture medium comprising greater than 0.15 mM but not more than 3.0 mM of a metal selected from the group consisting of cobalt, zinc and a mixture of cobalt and zinc.

2. A method according to claim 1 wherein the cholinesterase inhibitor is selected from the group consisting of diisopropylphosphoro-fluoridate, isopropylmethylphosphono-fluoridate and pinacolylmethylphosphono-fluoridate.

3. A method according to claim 1 wherein the culture medium in which the parathion hydrolase is produced comprises from 0.2 mM to 2.0 mM of said metal.

4. A method according to claim 3 wherein the concentration of said metal is 1 mM.

* * * * *